United States Patent [19]

Coburn

[11] Patent Number: 4,790,842

[45] Date of Patent: Dec. 13, 1988

[54] BLOOD SAMPLE SEGMENT DETACHING AND TEARING DEVICE

[76] Inventor: Timothy J. Coburn, 24 Fox Lane S., Palos Park, Ill. 60464

[21] Appl. No.: 91,125

[22] Filed: Aug. 31, 1987

Related U.S. Application Data

[63] Continuation-in-part of Ser. No. 907,316, Sep. 15, 1986, abandoned.

[51] Int. Cl.[4] .............................................. A61B 19/00

[52] U.S. Cl. .................................... 604/408; 604/411; 128/305; 128/329 R

[58] Field of Search ................................ 604/408–415, 604/86, 87, 280, 283, 162, 262; 128/305, 329 R, 760, 767, 346, 764; 222/85, 103

[56] References Cited

U.S. PATENT DOCUMENTS

| | | | |
|---|---|---|---|
| 2,896,619 | 7/1959 | Bellamy, Jr. | 604/409 |
| 3,323,208 | 6/1967 | Hurley, Jr. | 128/346 |
| 3,568,673 | 3/1971 | Cowley | 604/162 |
| 4,320,787 | 3/1982 | McMorrow | 604/404 |

*Primary Examiner*—C. Fred Rosenbaum
*Assistant Examiner*—Mark F. Colosimo
*Attorney, Agent, or Firm*—Laubscher & Laubscher

[57] ABSTRACT

A device for use in detaching a segment filled with blood from a blood transfusion bag and at the same time making a tear in the segment so that the blood contained therein can be extracted for test purposes is disclosed. The device comprises a unitary rigid structure molded from plastic and having a pair of channel shaped cavity sections hingedly interconnected and sized and shaped so as to fit around at least a portion of the sample segment to be removed along its length, with one cavity section on each side thereof. A pair of projections, each terminating in a sharp point, are formed on one of the cavity sections. One of the projections is positioned so that it penetrates and produces a tear in the end seal at the inner end of the sample segment when the sample segment is placed properly in the device and two cavity sections are closed around the sample segment, the tear enabling the sample segment to be easily pulled or broken off from the blood transfusion bag. The other projection is positioned so as to penetrate and produce a break in the sample segment itself so that the blood contained therein can be easily extracted.

8 Claims, 4 Drawing Sheets

BLOOD SAMPLE SEGMENT DETACHING AND TEARING DEVICE

BACKGROUND OF THE INVENTION

This patent application is a continuation-in-part of patent application Ser. No. 907,316 filed Sept. 15, 1986 now abandoned.

The present invention relates to a device for use in detaching a segment of plastic tubing filled with blood and sealed at the ends from a blood transfusion bag and at the same time making a tear in the segment so that the blood contained therein can be extracted.

In a number of medical procedures, it is often necessary for a patient to receive a supplementary quantity of blood. The administration of such a quantity of blood, transferred first from a donor to a storage device and then from the storage device to the patient (recipient), is known in the art as a blood transfusion. Although the transfusion of blood is widely practiced, the administration of blood from a donor to a recipient is far from indiscriminant. In fact, before a patient may receive a transfusion of blood from a donor, the blood to be transfused must be tested with a sample of the patient's blood to insure that the transfused blood will not precipate a transfusion reaction in the patient. This blood compatibility test, known as cross-matching, involves mixing together the red blood cell component of the blood from the donor with serum from the patient and, subsequently, assaying for any agglutination that may ensue. If the results of the cross-matching indicate that the blood to be transfused would, in fact, precipate a transfusion reaction in the patient, a quantity of blood from a different donor and which is compatible with that of the patient is sought.

Quantities of donated blood available for use in transfusions are commonly stored in blood transfusion bags. These bags are usually made of a plastic material such as polyvinylchloride and are sized to hold about 450 milliliters of blood. Each bag has an inlet port through which the blood is received from a donor and a pair of outlet ports through which the blood is dispensed to a patient. A length of plastic tubing on the order of about forty-five centimeters or longer extends out from the inlet port and provides a passageway for the blood from the donor to the bag.

In the past, an additional quantity of blood was extracted from the donor and stored in a separate container called a pilot tube. The blood contained in the pilot tube was then available for use in cross-matching with blood from a recipient.

The problem with this procedure of using a pilot tube to hold a sample of the same blood that is in the bag is that mis-identification of pilot tubes is relatively facile. For this reason, the practice of maintaining a small, sample sized volume of blood separate from the larger volume of blood to which it corresponded has been abandoned.

Instead, the presently utilized procedure has been implemented whereby, enough blood is extracted from the donor so as to fill both the blood transfusions bag and the length of plastic tubing at the inlet port. Then, using a dielectric sealer, the length of plastic tubing is divided into (i.e. sealed off at spaced apart locations along its length so as to form) a series or chain of about a dozen segments, each segment having about 2 ml. of the same blood that is in the plastic bag.

The advantage of using this procedure of making segments filled with blood from the length of tubing at the inlet port is that each segment is a sample sized volume of blood which can be detached from the plastic bag for cross-matching purposes at the time the blood is actually needed. As a result, there is little likelihood of a segment being misplaced or mis-identified. When a sample of blood is desired for testing, a technician will detach a segment, usually the segment most distal to the plastic bag, if several segments remain attached to the bag, or the segment connected directly to the inlet of the bag, if there is only one remaining segment. The detaching of the segment is achieved sometimes by simply twisting the seal at the inner end back and forth and at the same time pulling at the segment until it is broken off at the seal. More often than not, however, this does not work. Accordingly, in most cases the detaching is achieved by cutting through the seal at the inner end of the segment (but not through the segment itself) using a pair of scissors. In either case, once the segment has been detached, a cut or puncture is made in the segment either at one location so that blood may be squeezed or centrifuged out or at two locations (to overcome capillary adhesion) so that the blood contained therein will flow out freely (into a test tube or other container).

As can be appreciated, the detaching and subsequent puncturing of a segment so that the blood contained may be accessed and tested requires the use of scissors. A disadvantage with this arrangement is that the blood in the segment will often contaminate the scissors. In addition, the use of scissors as a means for accessing the blood contained in the segment often leads to considerable spillage of blood either while the cut is being made or while the open segment is being moved to the container for testing or while the contents are being extracted from the segment and, in general, is quite messy.

Accordingly, it is an object of this invention to provide a new and improved device for detaching a segment of plastic tubing have blood from a blood transfusion bag and creating an opening in the segment through which the blood contained therein may be extracted.

It is another object of the present invention to provide a device as described above which will simultaneously make a tear in the seal at the inner end of the segment and make a puncture in the segment itself.

It is still another object of the present invention to provide a device as described above which is inexpensive to manufacture, is easily mass-produced, is simple to operate, is compact, contains only one part and is disposable.

It is still another object of the present invention to provide a device as described above which eliminates the need for using scissors or other type of cutting instruments and which reduces the likelihood of content spillage.

It is a further object of this invention to provide a device for simultaneously making a break in a plastic segment filled with a liquid and a break in a heat seal formed at one end of the segment.

SUMMARY OF THE INVENTION

A device constructed according to the teachings of the present invention for use in detaching a segment of plastic tubing sealed at the ends and filled with blood from a blood transfusion bag and at the same time making a tear in the segment so that the blood contained therein can be extracted comprises a structure having first and second cavity sections made of rigid material and sized and shaped so that it can be positioned to fit around at least a portion of the segment and at least a portion of the seal at the inner end thereof with one cavity section on each side thereof, means on one of the cavity sections for producing a break in the seal at the inner end of the segment when said two cavity sections are placed in position around the sample segment and inner seal and closed together and means on one of the cavity sections for producing a tear in the sample segment at the same time.

Various features, objects, and advantages will appear from the description to follow. In the description, reference is made to the accompanying drawings which form a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which like reference numerals or characters represent like parts and wherein.

DETAILED DESCRIPTION OF PREFERRED EMBODIMENTS

The present invention relates to a device for use in detaching a segment of tubing filled with blood from a blood transfusion bag and at the same time making a tear in the segment so that the blood contained therein can be extracted. The present invention accomplishes this by providing a device having two cavity sections which are adapted to be placed in position around at least a portion of the segment and at least a portion of the seal on the inner end of the segment, one on each side thereof. The cavity sections include two specially shaped and positioned projections. One of the projections causes a break or tear in the seal at the inner end of the segment when the two cavity sections are closed around the segment and the inner seal and at the same time the other projection causes a break or tear in the segment itself.

Figure 1:
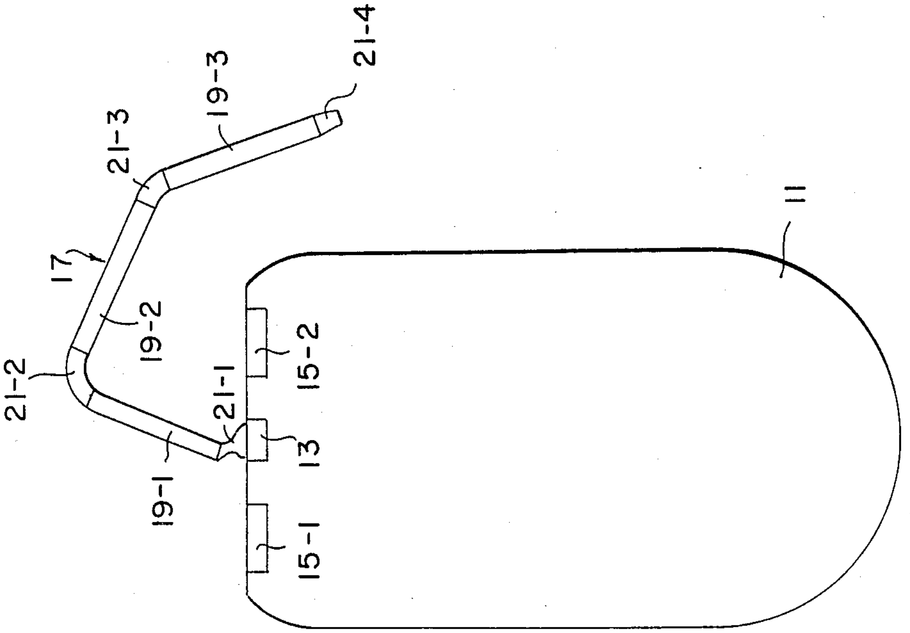
FIG. 1 is a front elevation view of a blood transfusion bag with a chain of sample segments attached thereto.
Figure 6:
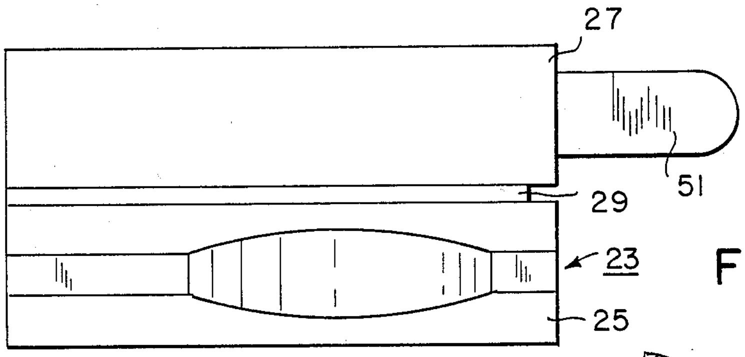
FIG. 6 is a plan view taken from the bottom of the segment detaching and tearing device shown in FIG. 2.
Figure 7:
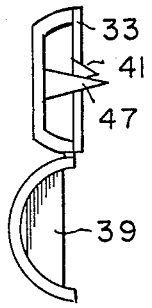
FIGS. 7 and 8 are left and right end views, respectively, of the segment detaching and tearing device shown in FIG. 2.
Figure 8:
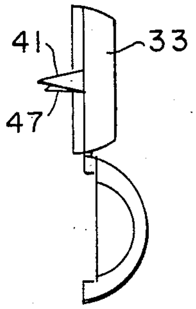
Figure 10:
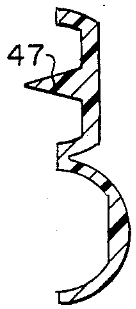
FIGS. 9, 10, 11 are section views taken along lines A—A, B—B and C—C, respectively, of the segment detaching and tearing device shown in FIG. 3.
Figure 9:
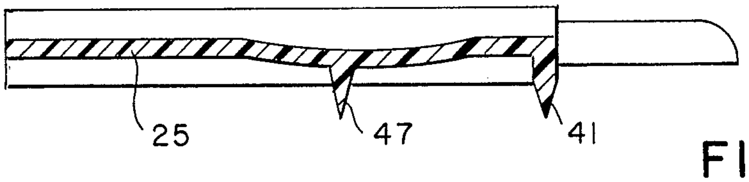
Figure 11:
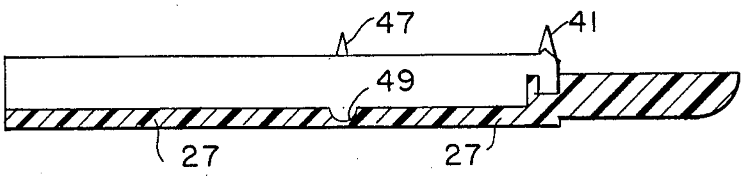

Referring to the drawings, there is illustrated in FIG. 1 a blood transfusion bag identified by reference numeral 11. Blood transfusion bag is made of a plastic material such as polyvinylchloride and is filled with blood (not shown) that has been extracted from a donor. Blood transfusion bag 11 includes an inlet port 13 through which blood enters the bag and a pair of outlet ports 15-1 and 15-2 through which blood leaves the bag. Extending out from inlet port 13 of blood transfusion bag 11 and integrally formed therewith is a length of plastic tubing 17 also filled with blood. Plastic tubing 17 is divided into a chain or series of segments, 19-1 through 19-3, the individual segments being separated from one another by seals (i.e. sealed areas) 21-1 through 21-4 produced by a dielectric heat sealer, one seal or seal area 21 being at each end of each segment 19. For convenience, only three segments 19 are shown in the chain.

For illustrative purposes, it will be assumed that segment 19-3 is to be removed from blood transfusion bag 11 (i.e. detached from the string of segments) and also punctured so that the blood inside the segment can be extracted.

Referring now to FIGS. 2-11 there is shown an embodiment of a sample segment detaching and tearing device constructed according to the teachings of the present invention and identified generally by reference number 23.

Figure 2:
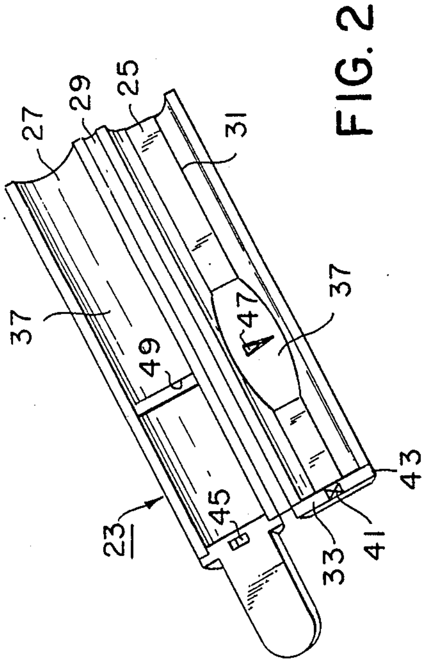
FIG. 2 is a perspective view of one embodiment of a segment detaching and tearing device constructed according to the teachings of the present invention with the two cavity sections in the open position.
Figure 3:
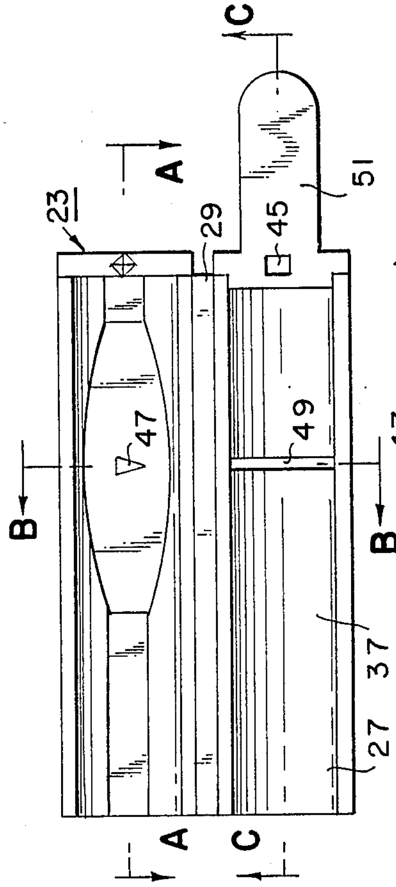
FIG. 3 is a plan view taken from the top of the segment detaching and tearing device shown in FIG. 2.
Figure 5:
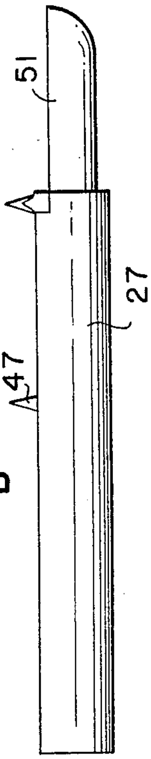
FIG. 5 is a rear elevation view of the segment detaching and tearing device shown in FIG. 2.
Figure 4:
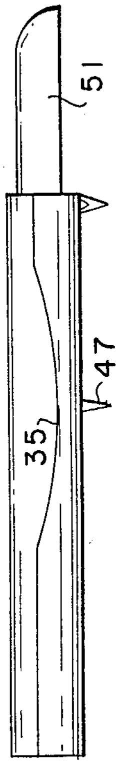
FIG. 4 is a front elevation view of the segment detaching and tearing device shown in FIG. 2.

As can be seen, especially in FIG. 2, device 23 comprises a unitary structure which is made entirely of a rigid plastic material capable of being molded to a sharp edge, such as polypropylene. Device 23 includes a first channel shaped cavity section 25 and a second channel shaped cavity section 27. The two cavity sections 25 and 27 are interconnected along their lengths in side-by-side relationship by a living hinge 29. Alternatively, the two cavity sections 25 and 27 may be hingedly joined together in end-to-end relationship. Device 23 is preferably smaller in length than a segment 19, so that when it is placed next to a segment and closed around it, it will only partly encompass it.

First cavity section 25 includes a curved semitubular bottom or main wall 31 and a semi-oval shaped end wall 33. Bottom wall 31 includes a central portion 35 which is recessed or flattened out on its outer surface for gripping purposes. Second cavity section 27 includes a semicylindrical bottom or main wall 37 and a semicircular end wall 39. Cavity sections 25 and 27 are sized so as to fit around at least a portion of a segment and at least a portion of the seal at the inner end of the segment when the device is positioned next to a segment with one cavity section on each side thereof.

A first projection 41, which is pyramidial and symmetrically shaped extends upward from the top surface 43 of end wall 33 of first cavity section 25. A rectangular slot 45 sized to accommodate the top of first projection 41 when device 23 is closed is formed on the top of end wall 39 of second cavity section 27. A second projection 47 which is also pyramidial shaped, extends upward from the recessed inner surface 37 of bottom wall 31 of cavity section 25. Second projection 47 is asymmetrical (i.e. the tip is off center) and is positioned off center from the longitudinal axis of section 25 so as to create a tear rather than a hole when it penetrates a segment as will hereinafter be explained. Cavity section 27 has a slot 49 on the inside surface of bottom wall 37 to accommodate the top of second projection 47 when device 23 is closed.

Cavity section 27 further includes a tongue depressor shaped stilt 51, which extends outwards from front end wall 39.

Figure 14:
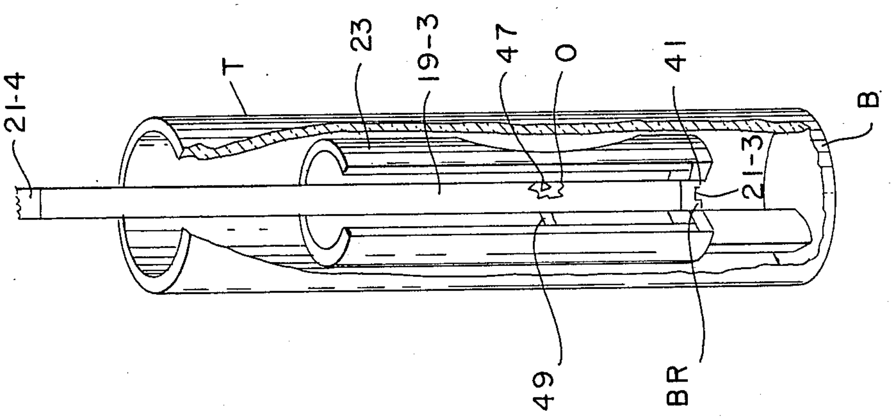
FIG. 14 is a perspective view partly broken away of the segment detaching and tearing device of FIG. 2 disposed in a test tube in a partially open position so that the blood contained in a segment within the device may be extracted.
Figure 12:
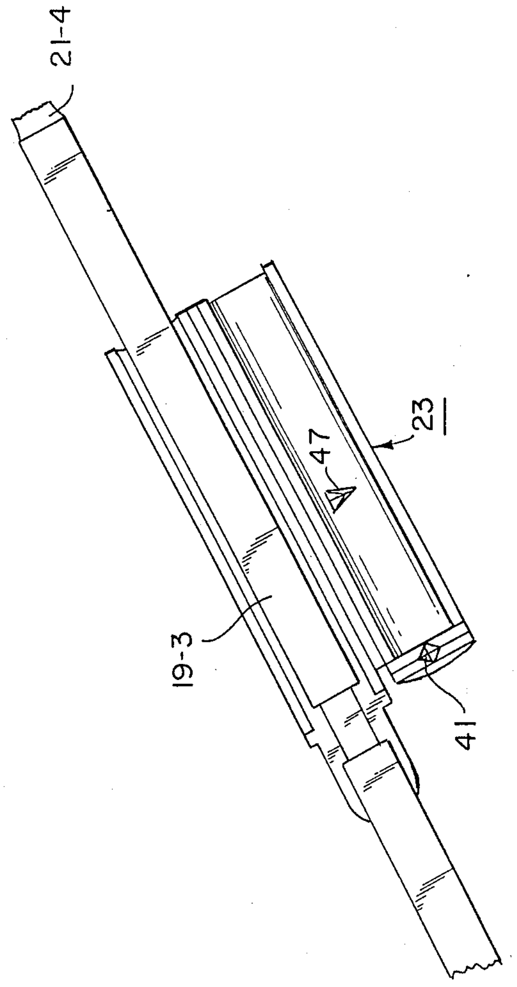
FIG. 12 is a perspective view taken from the top of the segment detaching and tearing device of FIG. 2 in the open position with a segment in position for detachment and puncturing.
Figure 13:
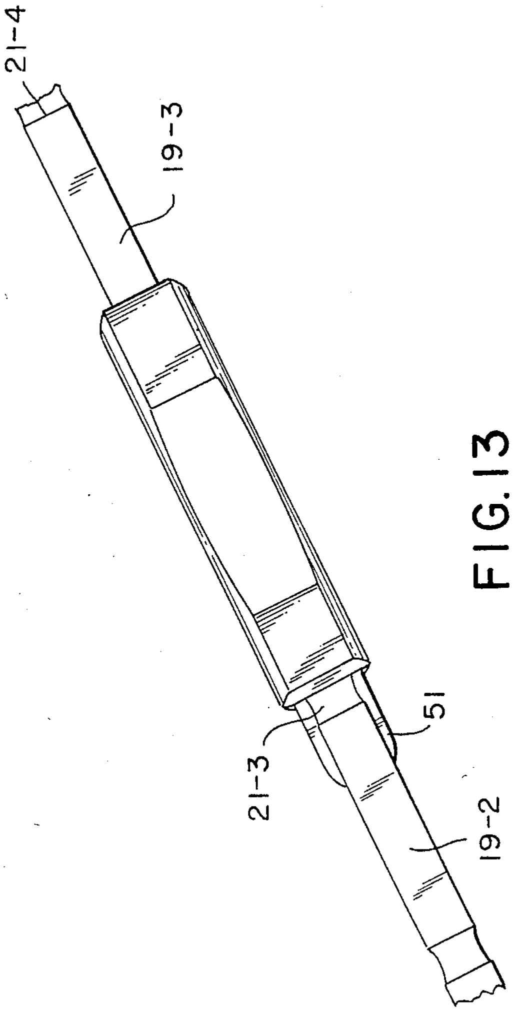
FIG. 13 is a perspective view taken from the bottom of the segment detaching and tearing device of FIG. 2 in the closed position with the segment to be detached and severed inside the device.
Figure 17:
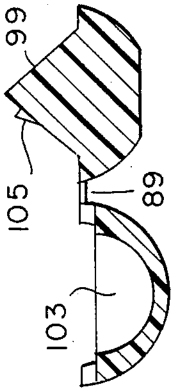
FIG. 17 is a section view taken along lines D—D in FIG. 16.
Figure 18:
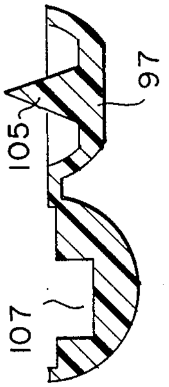
FIG. 18 is a section view taken along lines E—E in FIG. 16.
Figure 19:
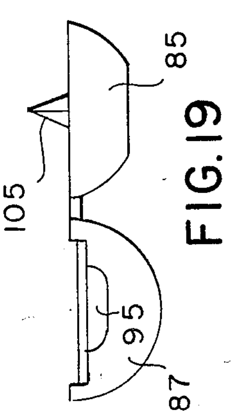
FIG. 19 is a right end view of the segment detaching and tearing device shown in FIG. 16, with the two cavity sections in the open position.

Referring now to FIGS. 12–14, the manner of using device 23 will now be explained. Assume that segment 19-3 of plastic tubing is to be detached and severed. First, segment 19-3 is placed on top of bottom wall 37 of cavity section 27 and positioned so that seal 21-3, which is at the inner end of segment 19-3 and is to be broken, lies directly above slot 43, as shown in FIG. 12 and thus in line to be punctured by projection 41 when the two cavity sections are closed. Device 23 is then closed by swinging cavity section 25 into contact with cavity section 27 as shown in FIG. 13. When device 23 is closed, projection 41 will cut through and make a break BR in seal 21-3 (but not segment 19-3) and penetrate into slot 45. At the same time, projection 47 will slash segment 19-3 and penetrate slot 49. Since seal 21-3 now has a break, segment 19-3 while still remaining inside the two cavity sections of device 23 can be easily broken off from bag 11.

Once segment 19-3 has been detached, the user may either open device 23 and remove segment 19-3 or place device 23 with sample segment 19-3 contained in the cavity defined by the two cavity sections into a test tube T. If the former approach is selected, segment 19 is squeezed so that the blood contained therein flows out of the opening O created by projection 47 and is then collected in a test tube T or other container. If the latter approach is selected, device 23, including segment 19-3, is placed into a test tube T with stilt 51 facing downward as shown in FIG. 14. Because there is no means for securing the two cavity sections of device 23 in the closed position, device 23 will open partially when it is placed in test tube T. Device 23 is placed into test tube T with stilt 51 facing downward so that a pool of blood B will form at the bottom of tube 39 during centrifugation and will not be capable of re-entering segment 19-3 once centrifugation stops. After the blood has been extracted, segment 19-3 is lifted out from test tube T carrying with it device 23 which is coupled to it through projection 47.

Figure 15:
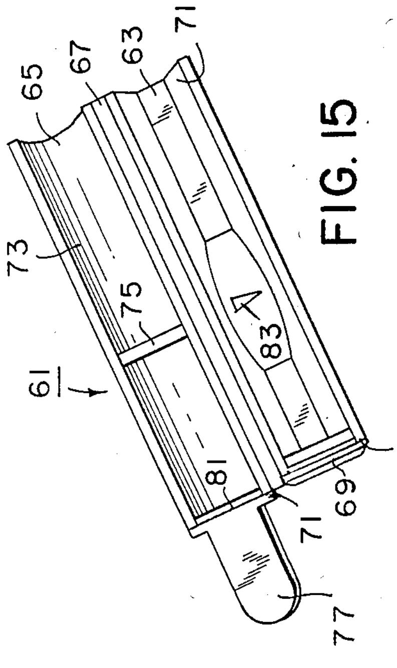
FIG. 15 is a perspective view of another embodiment of a segment detaching and tearing device constructed according to the teachings of the present invention, with the two cavity sections in the open position.
Figure 16:
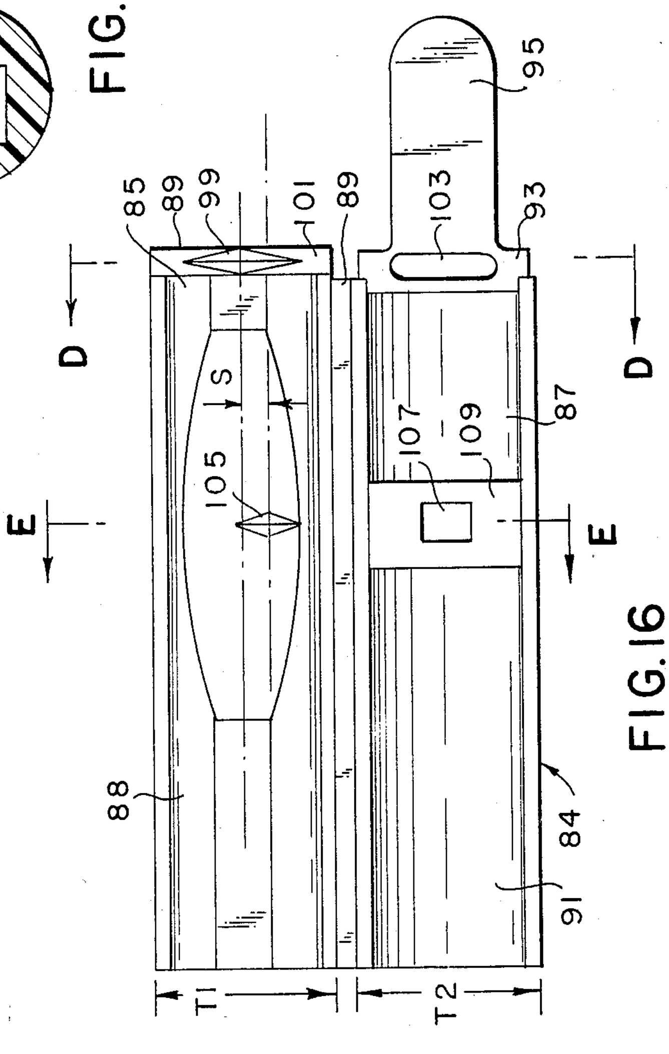
FIG. 16 is a plan view, taken from the top, of another embodiment of a segment detaching and tearing device constructed according to the teachings of the present invention, with the two cavity sections in the open position.

Referring now to FIG. 15, there is illustrated another embodiment of a device for detaching a segment from a blood transfusion bag and at the same time creating an opening in segment through which the blood contained therein may be extracted constructed according to the teachings of the present invention and identified generally by reference numeral 61. Device 61 is similar to device 23 in that it is a unitary rigid structure made of plastic and includes first and second cavity sections 63 and 65 connected by a living hinge 67. First cavity section 63 includes a semi-oval shaped end wall 69 and a curved bottom wall 71 having a projection 83. Second cavity section 65 includes a semicircular end wall 71, a curved bottom wall 73 having a slot 75 and a stilt 77. However, device 61 includes a knife edge 79 projection which extends upward from top surface of end wall 69, instead of a pyramidial shaped projection 41 as in the FIG. 2 embodiment, and an end wall 71 includes a knife edge slot 81 into which knife edge 79 penetrates when device 71 is closed, instead of a rectangular pyramidial receiving slot 43 as in the FIG. 2 embodiment.

Operation of device 61 is identical to that of device 23 the only difference being in the shape of the break produced by knife edge 79 of the FIG. 15 device and projection 41 of the FIG. 2 device and projection 41.

Referring now to FIGS. 16 through 20, there is shown another embodiment of a device constructed according to this invention and identified by reference numeral 84.

Device 84 is a unitary rigid structure made of a plastic such as polypropylene and includes first and second cavity sections 85 and 87, respectively, connected by a living hinge 89. Device 84 is sized so that when it is closed around a segment it will only partly encompass it, as in the FIG. 1 embodiment.

First cavity section 85 includes a semitubular shaped bottom wall 88, and a semi-oval shaped end wall 89. Second cavity section 87 includes a semitubular shaped bottom wall 91, a semicircular shaped end wall 93 and a stilt 95. Bottom wall 88 is flattened out on area 97 of its outer surface for gripping purposes.

Figure 20:
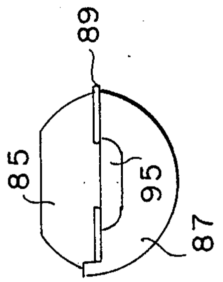
FIG. 20 is a right end view of the segment detaching and tearing device show in FIG. 16, with the two cavity sections in the closed position.

The transverse dimension T1 of first cavity section 85 is slightly smaller than the transverse dimension T2 of second cavity section 87 so that cavity section 85 overlaps cavity section 87 when the two cavity sections are closed as shown in FIG. 20 so as to reduce the likelyhood of blood dripping out when the device loaded with a segment is being moved by the user to the test tube.

A first projection 99, which is pyramidial and symmetrically shaped, extends upward from the top edge 101 of end wall 89 at the center and an oval shaped slot 103 sized to accommodate at least a portion of first projection 99 when device 84 is closed is formed opposite first projection 99 on end wall 93. A second projection 105, which is also pyramidial in shape, extends up from bottom wall 87. Projection 105 is asymmetrical and is disposed off center from the longitudinal axis of cavity section 85 by a small distance S so as to produce a tear rather than a hole when it penetrates a segment. A rectangular slot 107 sized to accommodate at least a portion of second projection 105 when device 83 is closed is formed opposite second projection 99 in an intermediate wall 109 extending upward from bottom wall 91.

Device 84 is used in the same way as device 23.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. In a blood transfusion bag including synthetic plastic tubing connected therewith, the tubing being heat sealed at spaced locations along its length to define successive sections filled with samples of the blood within the bag, apparatus for severing a blood sample segment from the tubing and for piercing said segment, comprising (a) a tubular housing defining a chamber for receiving a blood sample segment, said housing having a longitudinal axis and including first and second longitudinal sections each having a hemicylindrical configuration;

(b) hinge means for connecting said sections together along a longitudinal edge, whereby said sections are movable between open and closed positions;

(c) said first section including first and second spaced projection means extending transversely therefrom for defining sharp edges, respectively, said first projection means being arranged at one end of said first section and said second projection means being arranged intermediate the ends thereof; and (d) said second section containing first and second slots opposite said first and second projection means of said first section, respectively, said second section slots receiving said first section projection means when said sections are in the closed position, whereby when said sections are in the open position, a blood sample segment is arranged within said second section with a seal arranged at said one end, and when said sections are moved to the closed position to enclose said blood sample segment within said chamber, said first and second projection means simultaneously break and puncture the seal and blood sample segment, respectively.

2. Apparatus as defined in claim 1, wherein said housing sections and said hinge means comprise a unitary structure.

3. Apparatus as defined in claim 2, wherein said first and second sections each include a transverse wall at said one end, said first projection means extending from said first section end wall and said first slot being arranged in said second section end wall.

4. Apparatus as defined in claim 3, wherein said first projection means comprises a knife-edge for severing the seal of the blood sample segment.

5. Apparatus as defined in claim 4, wherein said second projection means terminates in a sharp point asymmetrically arranged relative to said first section.

6. Apparatus as defined in claim 5, and further comprising a stilt integrally connected with said one end of one of said housing sections adjacent said section end wall.

7. Apparatus as defined in claim 5, wherein the width of one of said housing sections is greater than the width of the other of said housing sections.

8. Apparatus as defined in claim 5, wherein said housing sections and said hinge means are formed of synthetic plastic material

* * * * *